United States Patent
Chen et al.

(10) Patent No.: US 11,105,943 B2
(45) Date of Patent: Aug. 31, 2021

(54) SYSTEM AND METHOD FOR MAPPING HYDROCARBON SOURCE ROCK USING SEISMIC ATTRIBUTES

(71) Applicant: Chevron U.S.A. Inc., San Ramon, CA (US)

(72) Inventors: Mingya Chen, Houston, TX (US); Fang Lin, Sugar Land, TX (US); Christopher H. Skelt, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 91 days.

(21) Appl. No.: 16/401,298

(22) Filed: May 2, 2019

(65) Prior Publication Data
US 2019/0339407 A1 Nov. 7, 2019

Related U.S. Application Data

(60) Provisional application No. 62/801,990, filed on Feb. 6, 2019, provisional application No. 62/666,143, filed on May 3, 2018.

(51) Int. Cl.
*G01V 1/30* (2006.01)
*G01V 1/28* (2006.01)
*G01N 33/24* (2006.01)
*G01V 99/00* (2009.01)

(52) U.S. Cl.
CPC .......... *G01V 1/306* (2013.01); *G01N 33/241* (2013.01); *G01V 1/284* (2013.01); *G01V 1/303* (2013.01); *G01V 1/307* (2013.01); *G01V 99/005* (2013.01); *G01V 2210/616* (2013.01)

(58) Field of Classification Search
CPC ........ G01V 1/284; G01V 1/303; G01V 1/306; G01V 1/307; G01V 2210/616; G01V 99/005; G01N 33/241; G06T 15/00
See application file for complete search history.

(56) References Cited

U.S. PATENT DOCUMENTS

| | | | |
|---|---|---|---|
| 8,612,156 B2 * | 12/2013 | Gulati | G01V 1/34 702/16 |
| 9,244,182 B2 | 1/2016 | Loseth et al. | |
| 10,120,092 B2 | 11/2018 | Chen et al. | |
| 2011/0108283 A1 * | 5/2011 | Srnka | G01V 11/00 166/369 |
| 2013/0064040 A1 * | 3/2013 | Imhof | G01V 1/302 367/73 |

OTHER PUBLICATIONS

Per Avseth et al: "Seismic screening for hydrocarbon prospects using rock-physics attributes", The Leading Edge, vol. 33, No. 3, Mar. 1, 2014 (Mar. 1, 2014), pp. 266-274, XP055611689.
(Continued)

*Primary Examiner* — Elias Desta
(74) *Attorney, Agent, or Firm* — Marie L. Clapp

(57) ABSTRACT

A method is described for identifying source rocks in a subsurface volume of interest. The method may include generating a trend-normalized reflectivity seismic attribute and calculating the location, thickness, organic richness and thermal maturity of the potential source rocks based on seismic data. The method may be executed by a computer system.

7 Claims, 21 Drawing Sheets

(56) References Cited

OTHER PUBLICATIONS

Brian Lecompte et al: "Quantifying Source Rock Maturity From Logs: How to Get More Than TOC From Delta Log R", SPE Annual Technical Conference and Exhibition, Jan. 1, 2010 (Jan. 1, 2010), XP055611957.

Atarita Thomas C et al: "Predicting Distribution of Total Organic Carbon (TOC) and S2with [Delta] Log Resistivity and Acoustic Impedance Inversion on Talang Akar Formation, Cipunegara Sub Basin, West Java", Procedia Engineering, Elsevier, Amsterdam, NL, vol. 170, Apr. 19, 2017 (Apr. 19, 2017), pp. 390-397, XP029975886.

Osareni Ogiesoba et al: "Seismic-attribute identification of brittle and TOC-rich zones within the Eagle Ford Shale, Dimmit County, South Texas", Journal of Petroleum Exploration and Production Technology, vol. 4, No. 2, Jun. 1, 2014 (Jun. 1, 2014), pp. 133-151, XP055611944.

PCT International Search Report and Written Opinion, dated Aug. 19, 2019, issued in International Application No. PCT/162019/053573, filed on May 2, 2019, 13 pages.

Løseth, Helge et al., "Can Hydrocarbon Source Rocks be Identified on Seismic Data?", Geological Society of America, Geology, Dec. 2011, pp. 1167-1170.

Vernik, Lev et al., "Rock Physics of Organic Shales", The Leading Edge, Mar. 2011, pp. 318-323.

Bandyopadhyay, Kaushik et al., "Rock Property Inversion in Organic-Rich Shale: Uncertainties, Ambiguities, and Pitfalls", SEG Las Vegas 2012 Annual Meeting, pp. 1-5.

Amato Del Monte A et al: "Methods for source rock identification on seismic data: An example from the Tanezzuft Formation (Tunisia)", Marine and Petroleum Geology, Butterworth Scientific, Guildford, GB, vol. 91, Dec. 15, 2017 (Dec. 15, 2017), pp. 108-124, XP085376120.

PCT International Search Report and Written Opinion, dated Aug. 19, 2019, issued in International Application No. PCT/162019/053572, filed on May 2, 2019, 13 pages.

* cited by examiner

=

−

SYSTEM AND METHOD FOR MAPPING HYDROCARBON SOURCE ROCK USING SEISMIC ATTRIBUTES

CROSS-REFERENCE TO RELATED APPLICATIONS

The present application claims priority from U.S. Provisional Patent Application No. 62/666,143 filed May 3, 2018 and U.S. Provisional Patent Application No. 62/801,990 filed Feb. 6, 2019.

STATEMENT REGARDING FEDERALLY SPONSORED RESEARCH OR DEVELOPMENT

Not applicable.

TECHNICAL FIELD

The disclosed embodiments relate generally to techniques for mapping hydrocarbon source rock in the earth's subsurface and, in particular, to a method of mapping hydrocarbon source rock quality and maturity using seismic attributes.

BACKGROUND

Seismic exploration involves surveying subterranean geologic media for hydrocarbon deposits. A survey typically involves deploying seismic sources and seismic sensors at predetermined locations. The sources generate seismic waves, which propagate into the geologic medium creating pressure changes and vibrations. Variations in physical properties of the geologic medium give rise to changes in certain properties of the seismic waves, such as their direction of propagation and other properties.

Portions of the seismic waves reach the seismic sensors. Some seismic sensors are sensitive to pressure changes (e.g., hydrophones), others to particle motion (e.g., geophones), and industrial surveys may deploy one type of sensor or both. In response to the detected seismic waves, the sensors generate corresponding electrical signals, known as traces, and record them in storage media as seismic data. Seismic data will include a plurality of "shots" (individual instances of the seismic source being activated), each of which are associated with a plurality of traces recorded at the plurality of sensors.

Recorded seismic data is commonly used to identify potential hydrocarbon reservoirs in reservoir rock (i.e., rock formations that contain the hydrocarbons). However, identifying reservoir rocks is only one piece of the hydrocarbon puzzle—there must also be source rocks in proximity to the reservoir rocks. Source rocks generate the hydrocarbons which may then migrate to reservoir rocks.

Conventional techniques for source rock characterization rely on well data and rock and fluid samples from wells and outcrops. Even where potential source rocks have been identified, lateral and vertical extrapolation of source rock properties beyond points of well/outcrop control relies on a simple assumption of the regional model, which often fail to predict source rock variability at basin and prospect scale adequately. Previous efforts have been made to use seismic data to map petroleum source rocks, by interpreting a strong negative amplitude as the top of the source rock. Recent publications have demonstrated that organic richness and thickness of sources sometimes may be mapped using acoustic impedance or by interpreting Class IV amplitude variation with offset (AVO) events. However, simply using acoustic impedance or Class IV AVO can lead to false positives in source rock identification and inaccurate prediction of source rock quality. In addition, none of the existing solutions remove the compaction effect that occurs when the rock layers are buried. Moreover, the existing solutions do not adequately demonstrate applicability of the techniques in terms of various thermal maturity or hydrocarbon generation potential of petroleum source rocks.

It is also desirable to determine the maturity of possible source rocks, since rocks that are not mature or that too mature may not be good hydrocarbon producers. As explained above, conventional techniques for source rock characterization rely on measurements using rock and fluid samples from wells and outcrops and estimations using well logs. Previous efforts to tackle the relationship between maturity and rock properties were focused on rock physics modeling and could only fit local data. The rock physics models did not take into consideration the intertwined effects on rock properties by increased mechanical and chemical compaction as source rocks become more mature and treated these factors as completely independent, which is not true.

The ability to define the location of source rock and reservoir rock in the subsurface is crucial to our ability to make the most appropriate choices for purchasing materials, operating safely, and successfully completing projects. Project cost is dependent upon accurate prediction of the position of physical boundaries within the Earth. Decisions include, but are not limited to, budgetary planning, obtaining mineral and lease rights, signing well commitments, permitting rig locations, designing well paths and drilling strategy, preventing subsurface integrity issues by planning proper casing and cementation strategies, and selecting and purchasing appropriate completion and production equipment.

There exists a need for improved source rock characterization in order to better assess potential hydrocarbon charge into the reservoirs.

SUMMARY

In accordance with some embodiments, a method of source rock characterization that receives a seismic dataset representative of a subsurface volume of interest and a low frequency model of the subsurface volume of interest; inverts the seismic dataset using the low frequency model to generate reservoir attributes; receives maturity data from core measurements or basin modeling; and characterizes the hydrocarbon source rock based on the reservoir attributes and maturity data is disclosed. The characterizing includes one or more of estimated TOC, source rock location, source rock thickness, and source rock maturity and the method may also generate a 2-D or 3-D map of the one or more of estimated TOC, source rock location, source rock thickness, and source rock maturity.

In another aspect of the present invention, to address the aforementioned problems, some embodiments provide a non-transitory computer readable storage medium storing one or more programs. The one or more programs comprise instructions, which when executed by a computer system with one or more processors and memory, cause the computer system to perform any of the methods provided herein.

In yet another aspect of the present invention, to address the aforementioned problems, some embodiments provide a computer system. The computer system includes one or more processors, memory, and one or more programs. The one or more programs are stored in memory and configured to be executed by the one or more processors. The one or more programs include an operating system and instructions that when executed by the one or more processors cause the computer system to perform any of the methods provided herein.

BRIEF DESCRIPTION OF THE DRAWINGS

Like reference numerals refer to corresponding parts throughout the drawings.

DETAILED DESCRIPTION OF EMBODIMENTS

Figure 1:
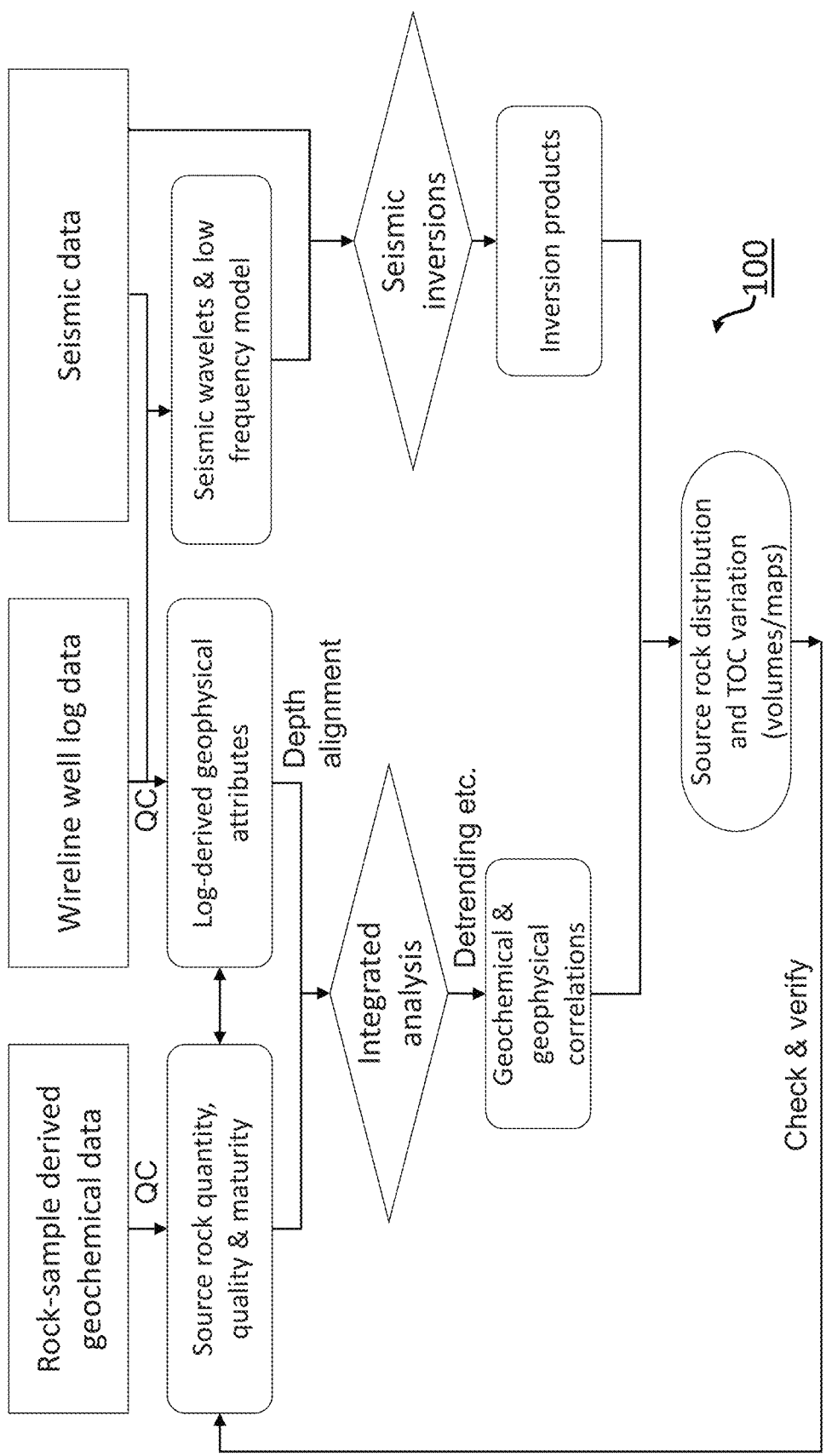
FIG. 1 illustrates a flowchart of a method of source rock characterization, in accordance with some embodiments.

Described below are methods, systems, and computer readable storage media that provide a manner of source rock identification and characterization. These embodiments are designed to be of particular use for identifying and characterizing hydrocarbon source rocks based on seismic data in addition to well data.

Reference will now be made in detail to various embodiments, examples of which are illustrated in the accompanying drawings. In the following detailed description, numerous specific details are set forth in order to provide a thorough understanding of the present disclosure and the embodiments described herein. However, embodiments described herein may be practiced without these specific details. In other instances, well-known methods, procedures, components, and mechanical apparatus have not been described in detail so as not to unnecessarily obscure aspects of the embodiments.

The present invention is a workflow for mapping petroleum source rocks, using rock-sample derived geochemical data, well log data, and seismic data as input. We systematically investigated the impact of depth of burial on source rock geophysical attributes, such as acoustic impedance (AI) and ratio of compressional velocity and shear velocity (Vp/Vs). We also investigated the impact of other geologic factors, such as source rock thickness, hydrocarbon generation potential, source rock distribution pattern, exhumation amount, hydrocarbon saturation level etc., on the aforementioned source rock geophysical attributes. Based on results from the above work, the present invention generates a new seismic attribute Trend-Normalized Reflectivity for source rock mapping. When combined with inverted Vp/Vs, this attribute is used to map the variation of organic richness and thickness of the petroleum source rock in two-dimensional cross section, or three-dimensional volume with confidence when data quality is adequate.

The present invention may further include a technique which brings maturity into the equation for predicting Total Organic Carbon (TOC) using geophysical properties. We analyzed data from both conventional source rocks and unconventional reservoirs. We systematically investigated the impact of kerogen content and thermal maturity on geophysical properties including velocity, density, acoustic impedance (AI) and ratio of compressional velocity and shear velocity (Vp/Vs). In contrary to what rock physics models suggested in published literature, our data show that acoustic impedance increases with increased thermal maturity of the rocks, likely due to complex physio-chemical compaction effect as rocks get buried deeper. Based on these data, we derived empirical relationships between AI, TOC, and thermal maturity, which united regional source rock prediction from seismic methods into a globally-applicable approach. The new approach enables us to predict TOC using seismically-inverted AI volume and maturity data derived either from core measurements or from basin modeling results. This method enables us to predict TOC when exhumation and erosion history is complex and depth-dependent compaction trends could not be established from data, and as such the first method described above could not be effectively applied. Meanwhile, it also provides a novel method to estimate thermal maturity of source rocks if TOC and geophysical properties of the source rocks are known.

The present invention could have large impacts on many exploration and development projects where source rock presence and distribution is a concern. It could substantially reduce the uncertainty associated with source rock presence and quality in a region, in turn contribute to proper assessment of hydrocarbon charge risk in exploration projects, leaving the era of heavy reliance on sparse well data behind. For appraisal and development projects, it could also help to assess the remaining and undiscovered resources by providing foundational data to calculate original oil- and/or gas-in-place (OOIP/OOGP) with higher confidence. The maturity prediction application may be particularly useful for Devonian and older source rocks, where traditional vitrinite reflectance method for thermal maturity determination is difficult to be applied due to lack of tree development in the Earth's early history.

FIG. 1 illustrates a flowchart for a comprehensive method of source rock characterization. The method 100 generates maps of the source rock locations. The method 100 takes as input geophysical data (seismic data) and well data (rock-sample derived geochemical data and wireline well log data). The well data, after appropriate quality control (QC), can be used to estimate source rock attributes (i.e., quantity, quality, and maturity) and log-derived geophysical attributes (with proper depth alignment and information from the seismic data). Integrated analysis of the source rock attributes and log-derived geophysical attributes, with necessary detrending, generate geochemical and geophysical correlations. The seismic data can be inverted based on the seismic wavelet and a low-frequency model. The seismic inversion products and the geochemical and geophysical correlations can be used to generate maps and/or volumes of the source rock distribution and Total Organic Content (TOC) variation in the subsurface volume of interest.

Figure 2:
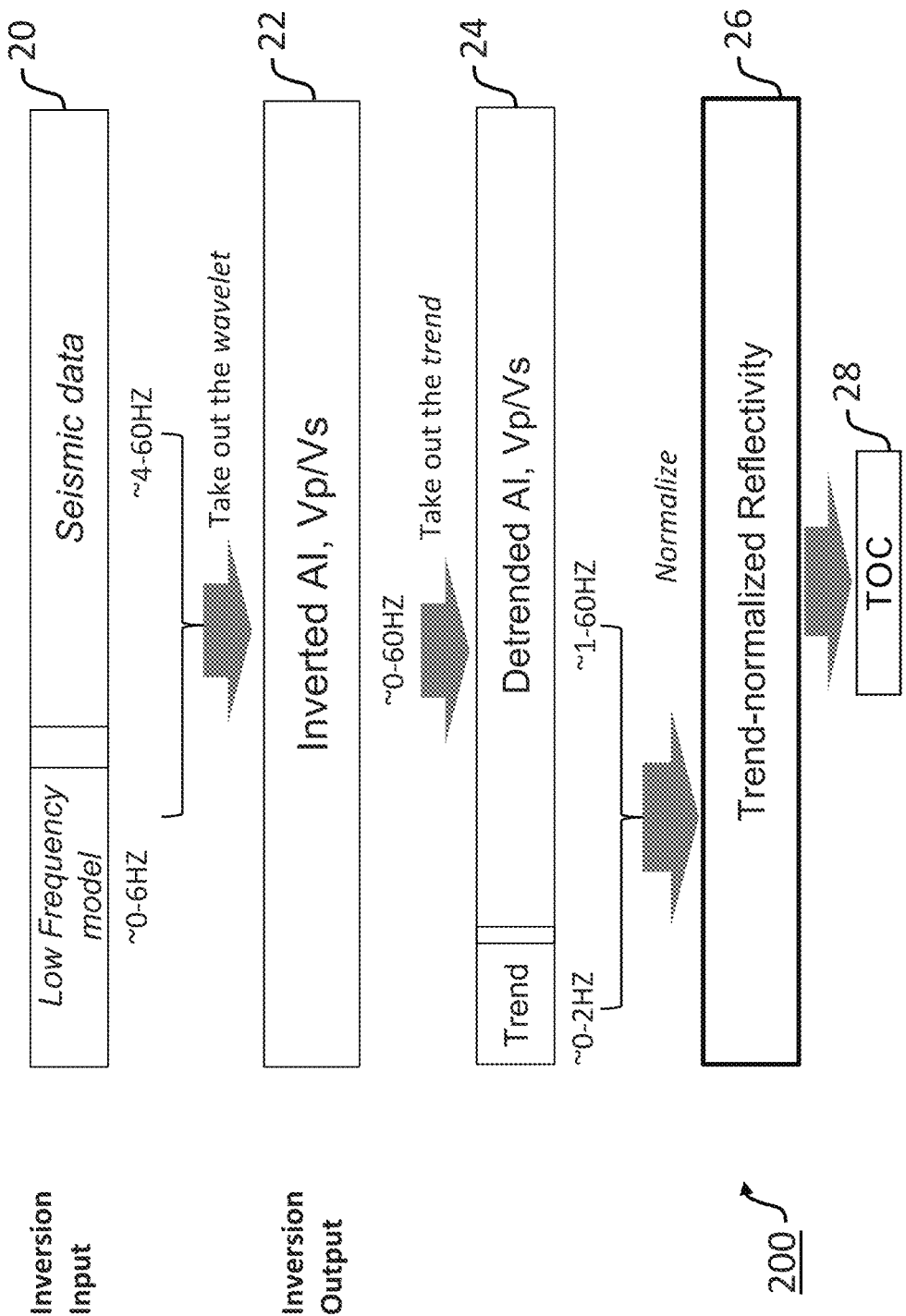
FIG. 2 illustrates a flowchart of steps in a method of source rock characterization, in accordance with some embodiments.

FIG. 2 illustrates a flowchart for a method 200 of using seismic inversion and detrending to generate an estimate of TOC. Seismic inversion methods attempt to convert seismic data into subsurface attributes such as acoustic impedance (AI), compressional velocity ($V_p$), shear velocity ($V_s$), density ($\rho$), and the like. AI in the subsurface formation is defined as:

$$AI = V_p \times \rho$$

Seismic reflections, which are recorded in seismic data, occur at layer boundaries due to the contrast in acoustic impedance (AI) of the layer above (layer 1) and below (layer 2). The reflection coefficient ($R_c$) at zero incident angle can be expressed as:

$$R_c = \frac{AI_2 - AI_1}{AI_2 + AI_1}$$

Figure 3:
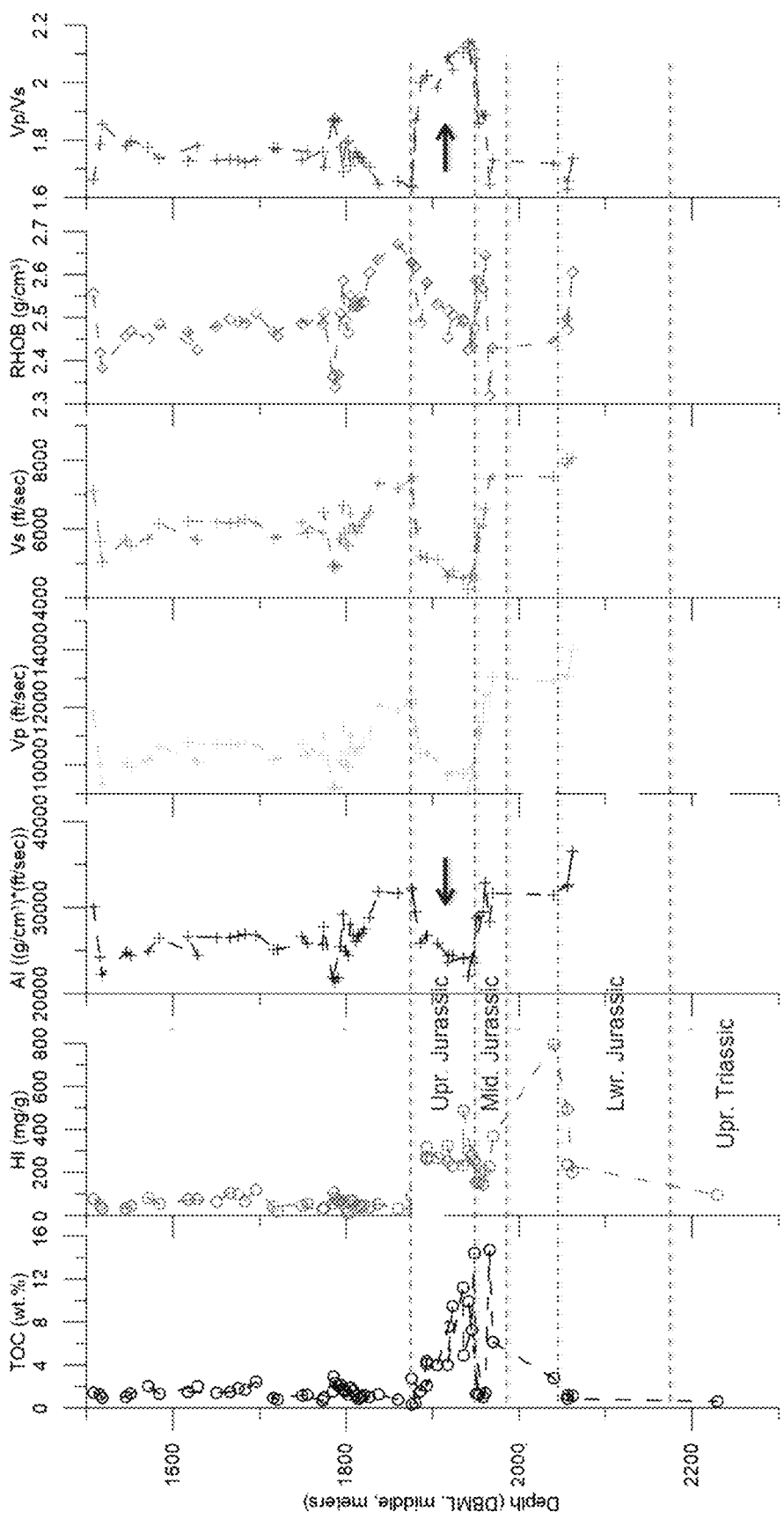
FIG. 3 demonstrates relationships between reservoir properties.

Factors that can affect AI include porosity, fluid saturation, lithology, compaction (temperature, stress, pore pressure), and organic content. Those of skill in the art will recognize that it is likely there will be a reduction in AI in high TOC shales as Kerogen is significantly less dense than common minerals such as quartz or clay minerals. This is shown in FIG. 3 where increasing TOC is accompanied by a decrease in AI, Vp, Vs, and density and an increase in Vp/Vs ratio, as indicated by the arrows.

Figure 4:
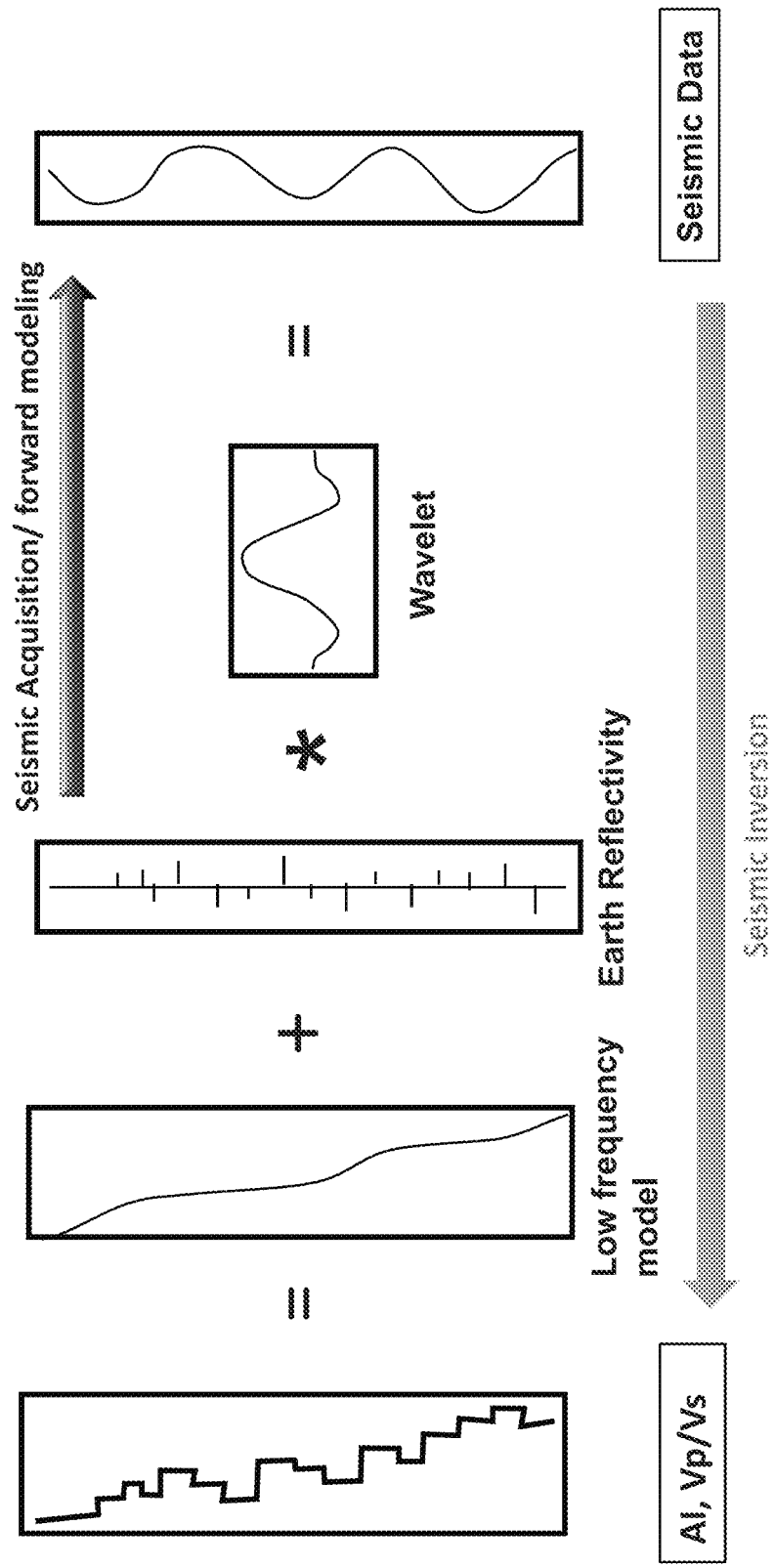
FIG. 4 demonstrates relationships between reservoir properties and seismic data.

Referring again to FIG. 2, the inversion input 20 includes the seismic data, which by way of example and not limitation contains frequencies between 4-60 Hz, and a low frequency model such as an initial earth model containing attributes such as $V_p$. Those of skill in the art will know that there are a variety of seismic inversion methods but they all have the effect of removing the wavelet from the seismic data and producing inversion output 22 which, again by way of example and not limitation, may be AI, $V_p$, $V_s$, or some combination such as $V_p/V_s$. FIG. 4 is a schematic depiction of how the reservoir attributes such as AI and $V_p/V_s$ are related to the seismic data by the low frequency model, the earth reflectivity, and the wavelet.

Figure 5:
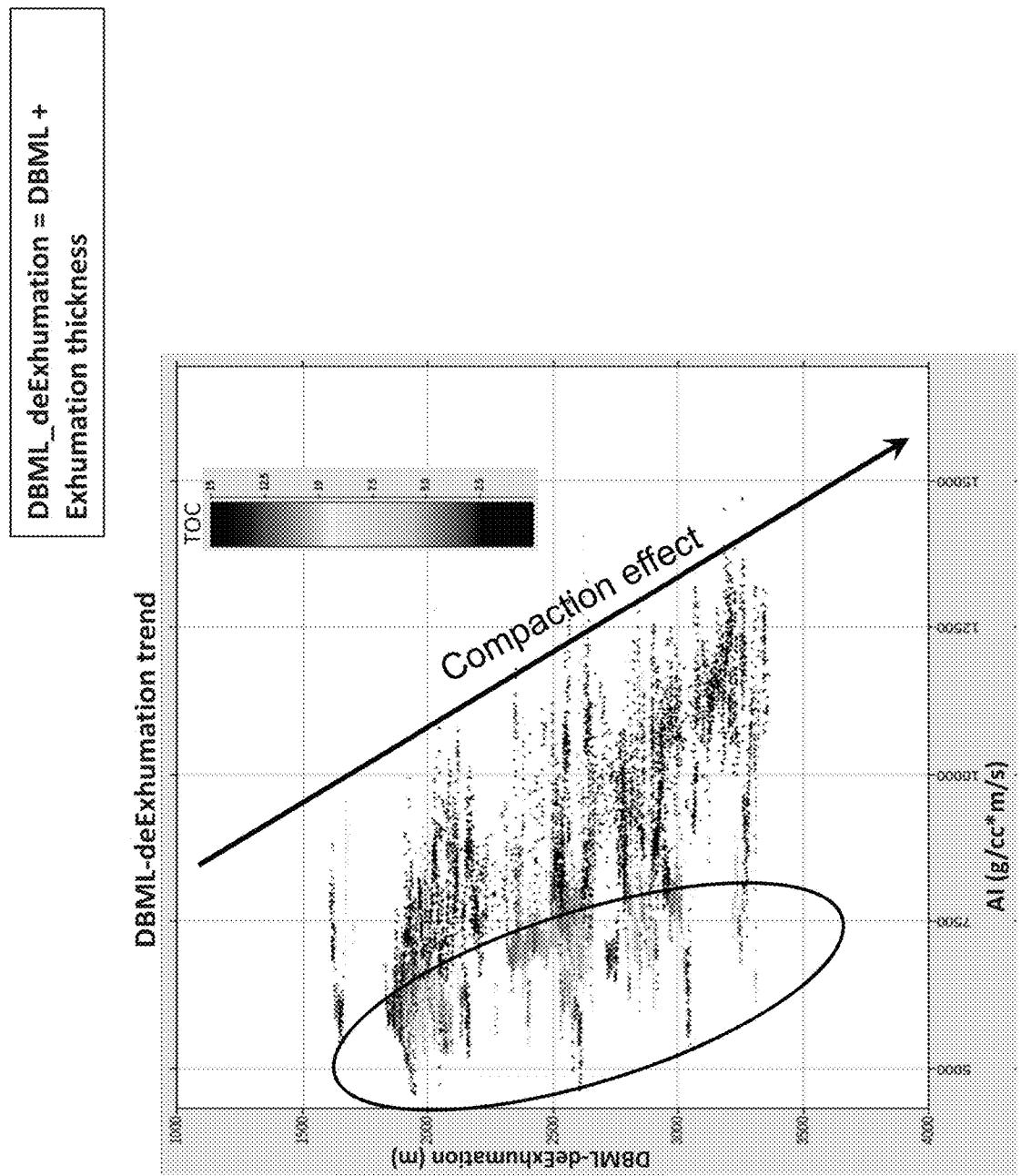
FIG. 5 demonstrates relationships of reservoir properties with depth.
Figure 6:
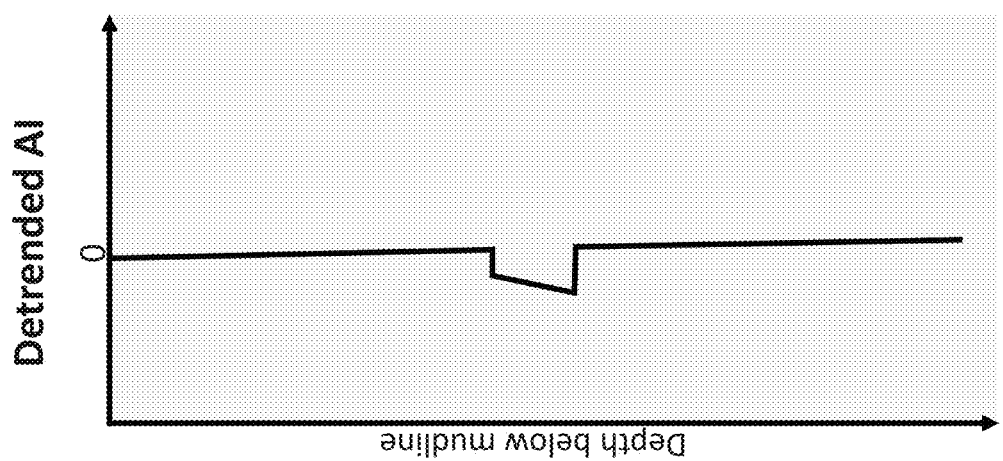
FIG. 6 demonstrates effects of a step in a method of source rock characterization.
Figure 6:
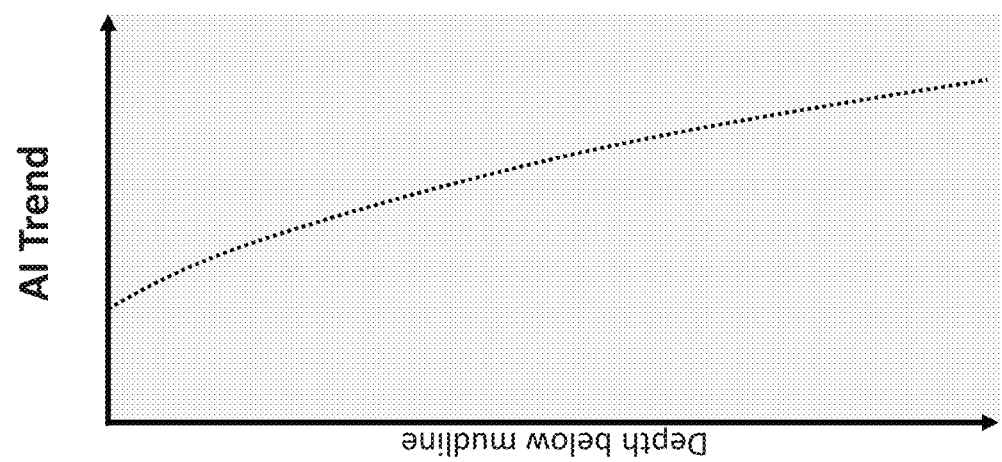
Figure 6:
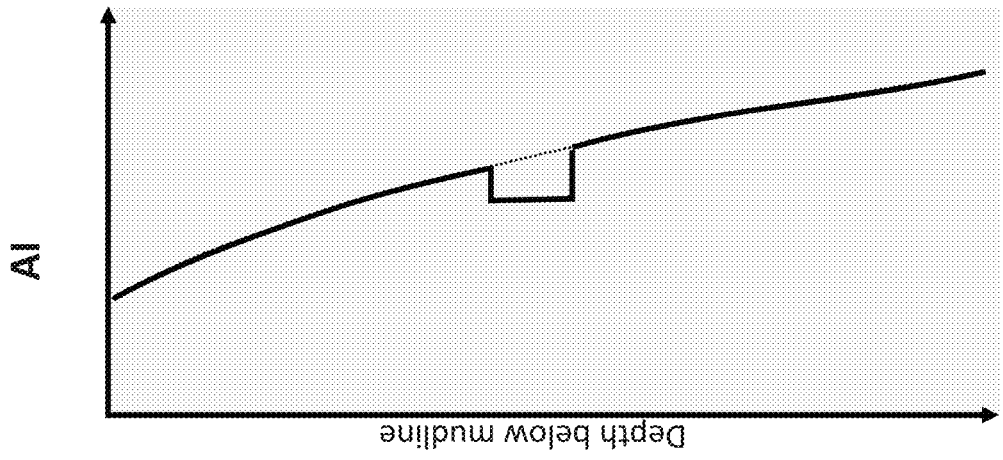
Figure 7:
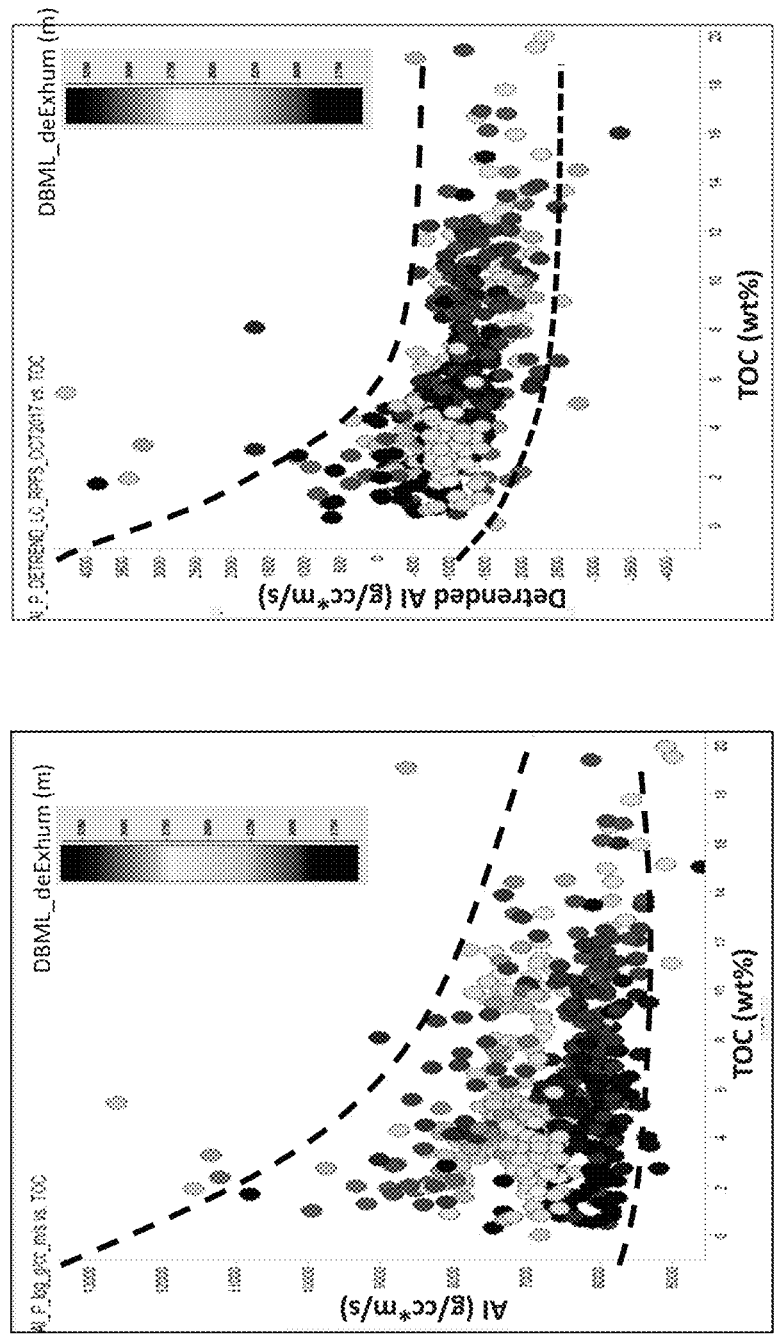
FIG. 7 demonstrates effects of a step in a method of source rock characterization.

FIG. 5 demonstrates that the AI increases with depth due to compaction effects. As rock formations are buried, the pressure of the overburden affects reservoir attributes such as density which affects the AI. FIG. 6 is a schematic representation of the process of detrending. The trends may be derived, for example, by identifying trends in well logs representing AI in rocks formations that are non-source rock shale (i.e., containing little solid organic matter) or by applying a lowpass filter (e.g., 0-2 Hz low pass) to well logs regardless of the type of rock they pass through. As shown in FIG. 7, when trying to determine the relationship of AI to TOC, the effects of the compaction trend result in no clear relationship (left crossplot) while after the trend is removed (right crossplot), a relationship becomes clear. Referring again to FIG. 2, the inversion output 22 is detrended to produce detrended AI and. optionally, $V_p/V_s$ and the trend itself. These can then be normalized to generate the trend-normalized reflectivity 26. Trend-normalized reflectivity mimics normal reflectivity terms. It is a simplified reflectivity when encased in a background rock. The normalization may be expressed as:

$$\text{Trend normalized reflectivity} = \frac{\text{Detrended } AI}{(\text{Background } AI \text{ trend}) \times 2}$$

Referring again to FIG. 2, the trend-normalized reflectivity 26 can be used to generate an estimate of TOC 28. The relationship between trend-normalized reflectivity and TOC is first determined using well data (including logs and TOC measurements from rock samples). This is demonstrated in FIG. 8. Then the trend-normalized reflectivity volume can be derived from detrending of seismically inverted volumes using the equation listed above. TOC is then predicted from the trend-normalized reflectivity volume using the relationship derived from wells.

Figure 8:
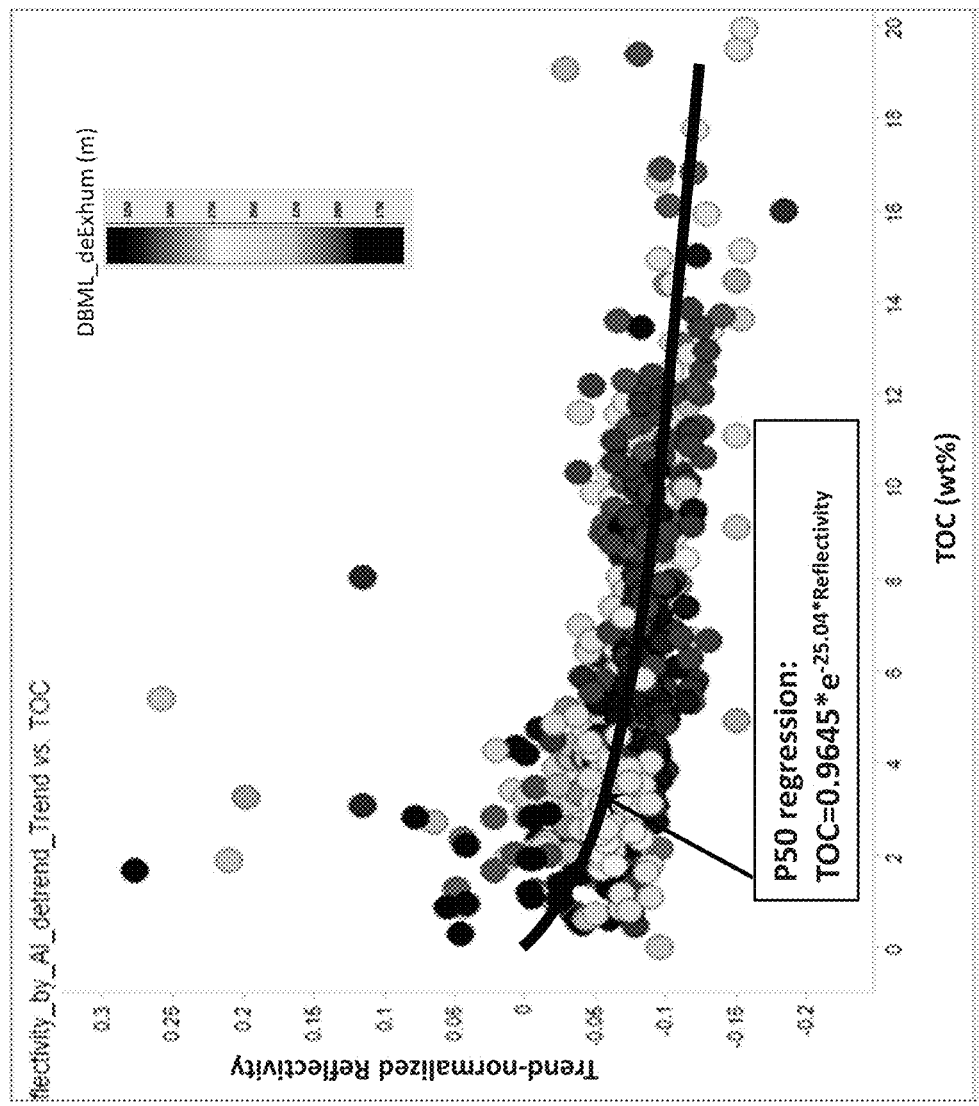
FIG. 8 demonstrates effects of a step in a method of source rock characterization.
Figure 9:
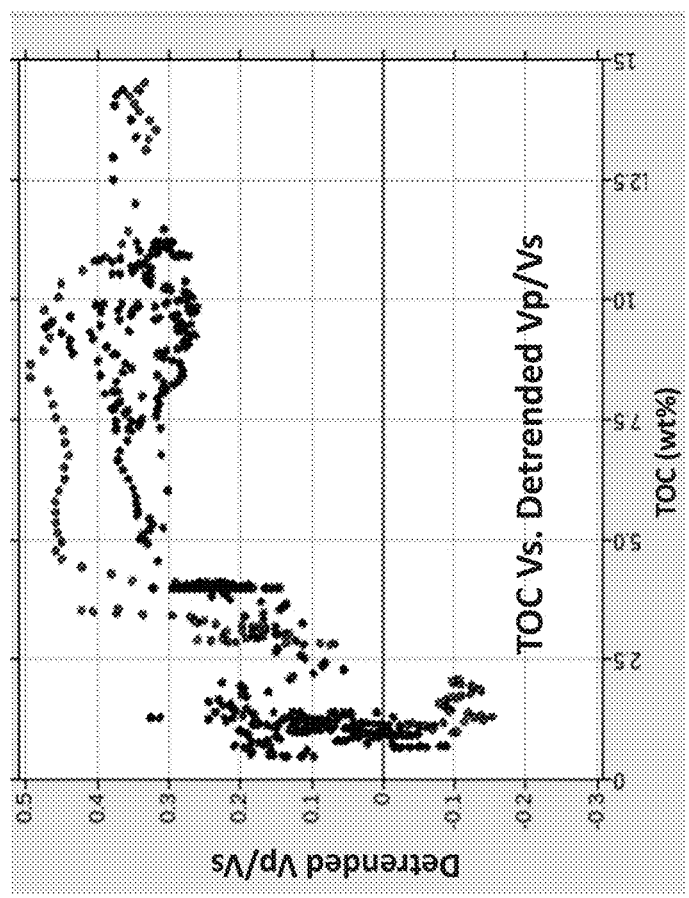
FIG. 9 demonstrates effects of a step in a method of source rock characterization.

In addition to deriving the AI, it is possible to derive the detrended $V_p/V_s$. As shown in FIG. 8, detrended $V_p/V_s$ appears to increase with TOC which is in contrary to what has been documented in most of the literature. To evaluate the relationship with TOC and $V_p/V_s$, additional data including XRD (X-ray diffraction) data measurements should be taken into consideration. FIG. 9 demonstrates that the detrended $V_p/V_s$ increases with increasing TOC which is the opposite of the observations seen in conventional analysis of $V_p/V_s$.

Figure 10:
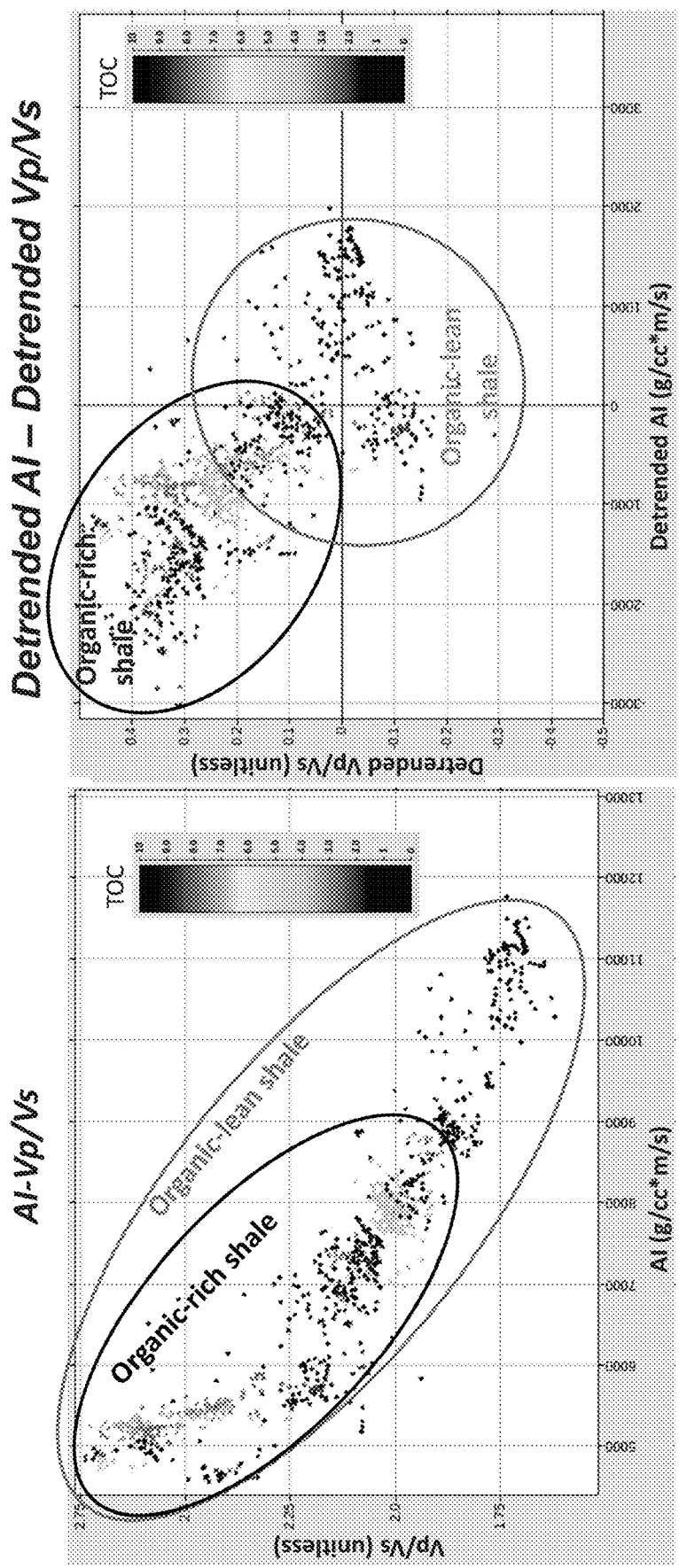
FIG. 10 demonstrates effects of a step in a method of source rock characterization.
Figure 11:
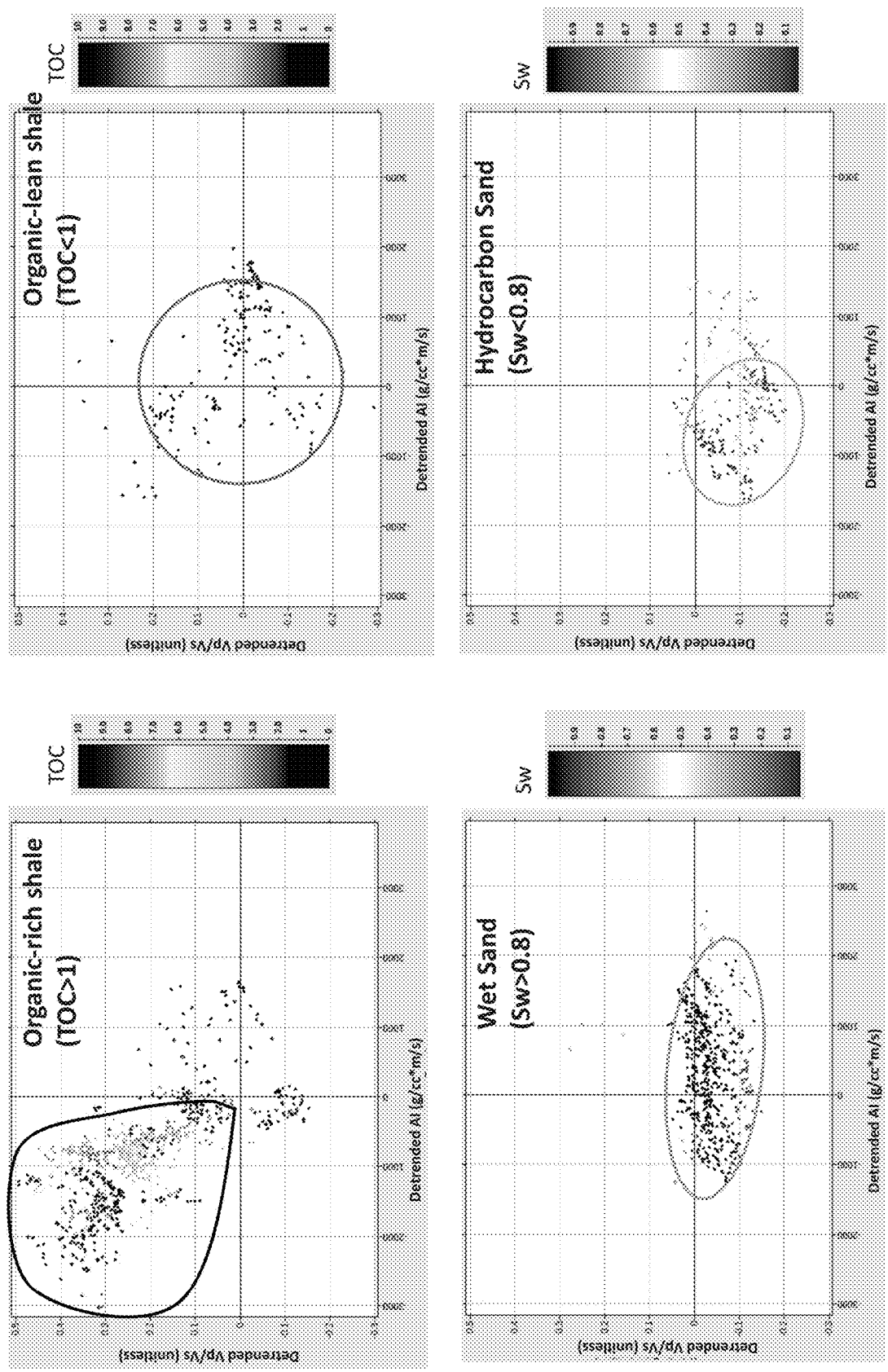
FIG. 11 demonstrates effects of a step in a method of source rock characterization.
Figure 12:
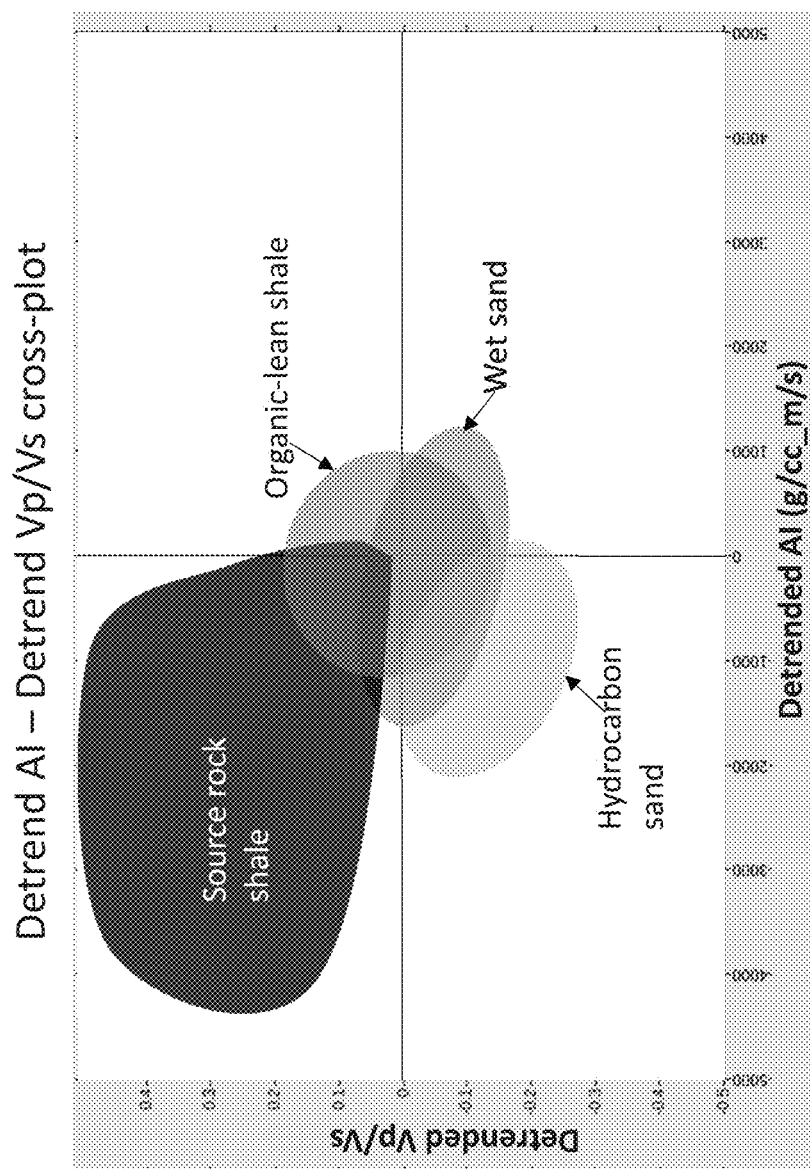
FIG. 12 demonstrates effects of a step in a method of source rock characterization.

FIG. 10 demonstrates the usefulness of the detrended AI and detrended $V_p/V_s$. On the left, a conventional AI vs. $V_p/V_s$ crossplot shows that the data points for the organic-rich shale and organic-lean shale overlap and cannot be distinguished from each other. Comparing this with the crossplot on the right, the detrended AI vs. detrended $V_p/V_s$ shows that the organic-rich shale can be distinguished from organic-lean shale, due to the unexpected result shown in FIG. 9 of the detrended $V_p/V_s$ increases with increasing TOC. This result makes the present invention a powerful new tool for source rock characterization. This is further illustrated in FIG. 11 and FIG. 12, which show detrended AI vs. detrended $V_p/V_s$ for TOC data for organic-rich shale and organic-lean shale and water saturation ($S_w$) data for wet sand (sandstone containing brine water) and hydrocarbon sand (sandstone containing hydrocarbons). The four crossplots seen in FIG. 11 are overlain in FIG. 12, illustrating the separation of the four different types of rock formation.

Figure 13:
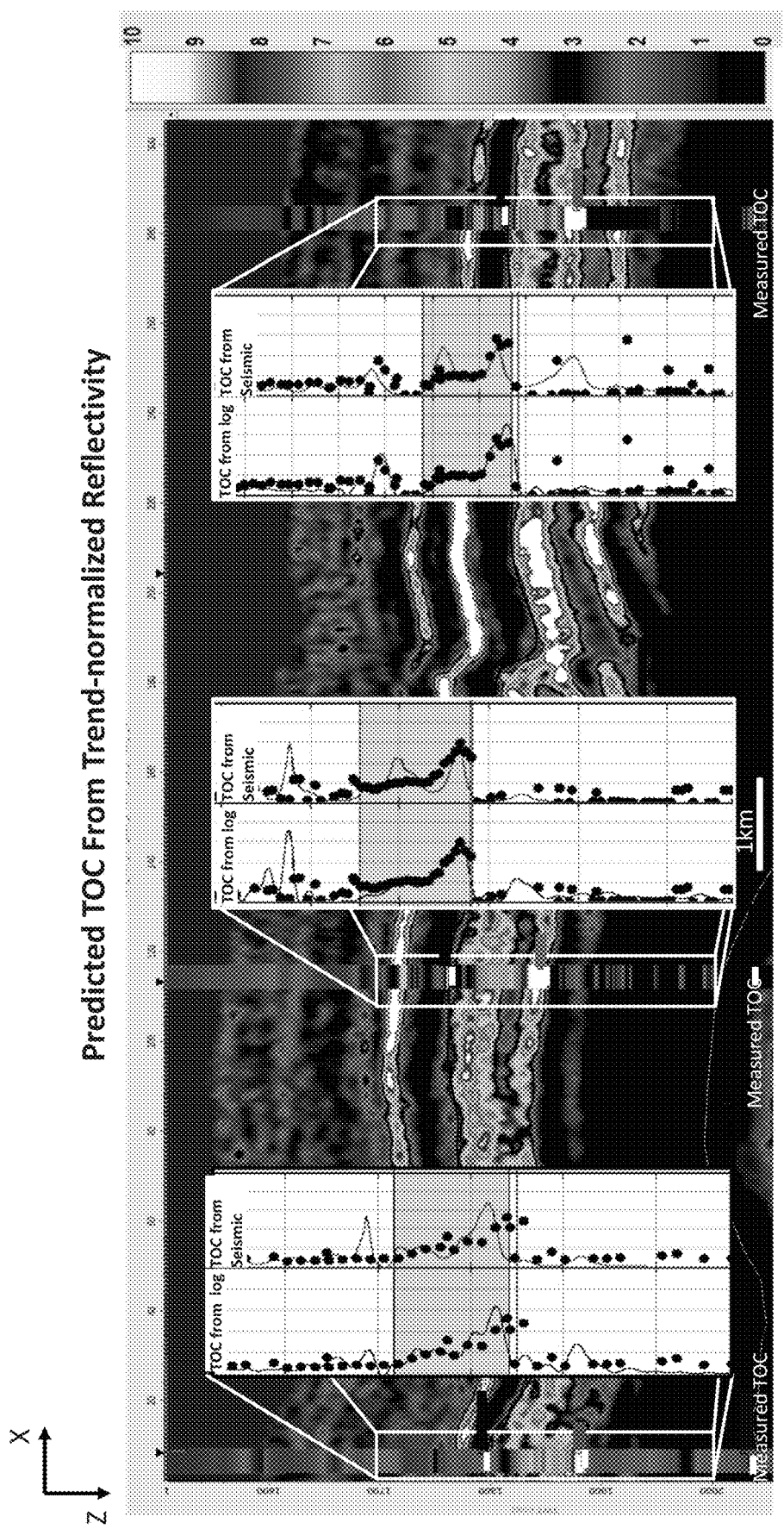
FIG. 13 illustrates a result of embodiments of the present invention.
Figure 14:
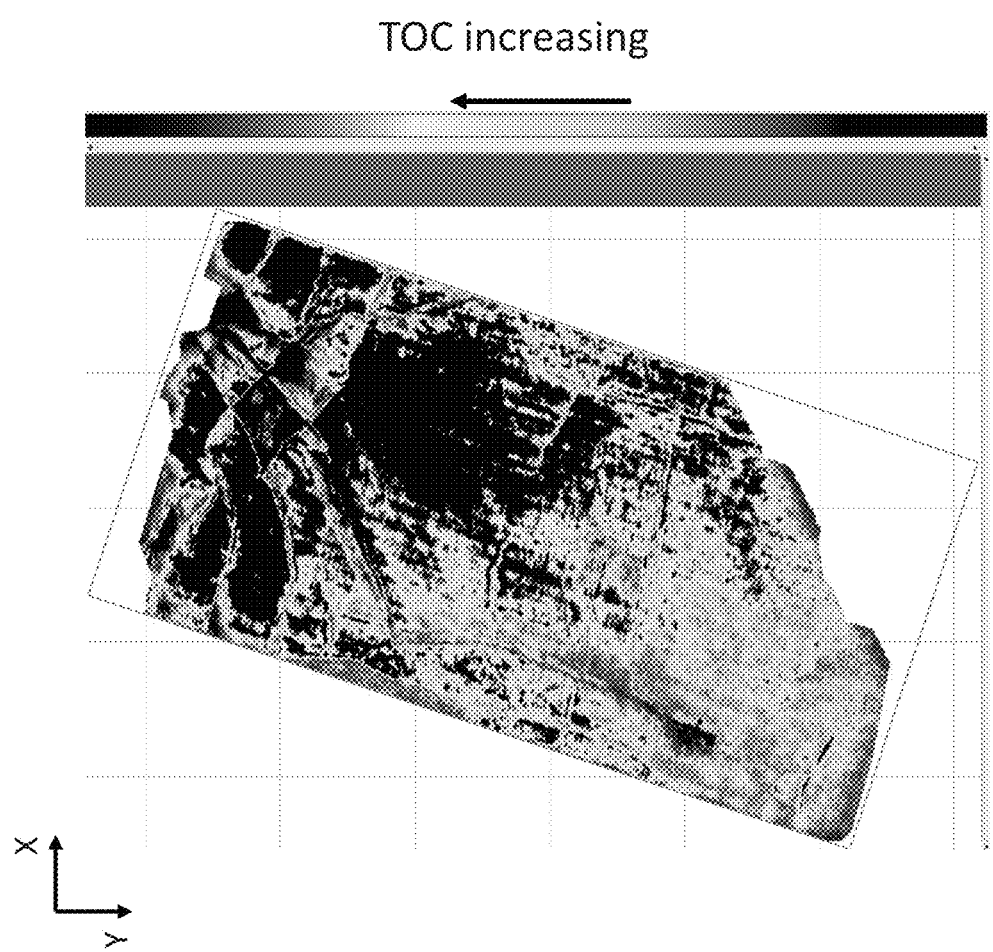
FIG. 14 illustrates a result of embodiments of the present invention.

FIG. 13 shows a 2-D section of the TOC volume generated by the method 200 with three comparisons of the TOC found at wells against the TOC derived from the seismic data. As can be seen, the seismically-derived TOC at the well locations matches accurately with the well log TOC. This allows confidence in the source rock mapping throughout the TOC volume generated by method 200. A plane-view map of TOC can be seen in FIG. 14. The ability to derive source rock maps from seismic data directly impacts hydrocarbon field management including well placement and perforation.

The present invention generates 2-D sections and/or 3-D volumes of estimated TOC for a subsurface volume of interest, allowing the mapping of source rock stratigraphic location and distribution. This includes information about the thickness of the source rock. The present invention can further provide information about probable range of organic richness (e.g., TOC<2%, 2-5%, >5% etc.). It is suitable for unconventional plays (shales) and for calcareous source rocks.

Figure 15:
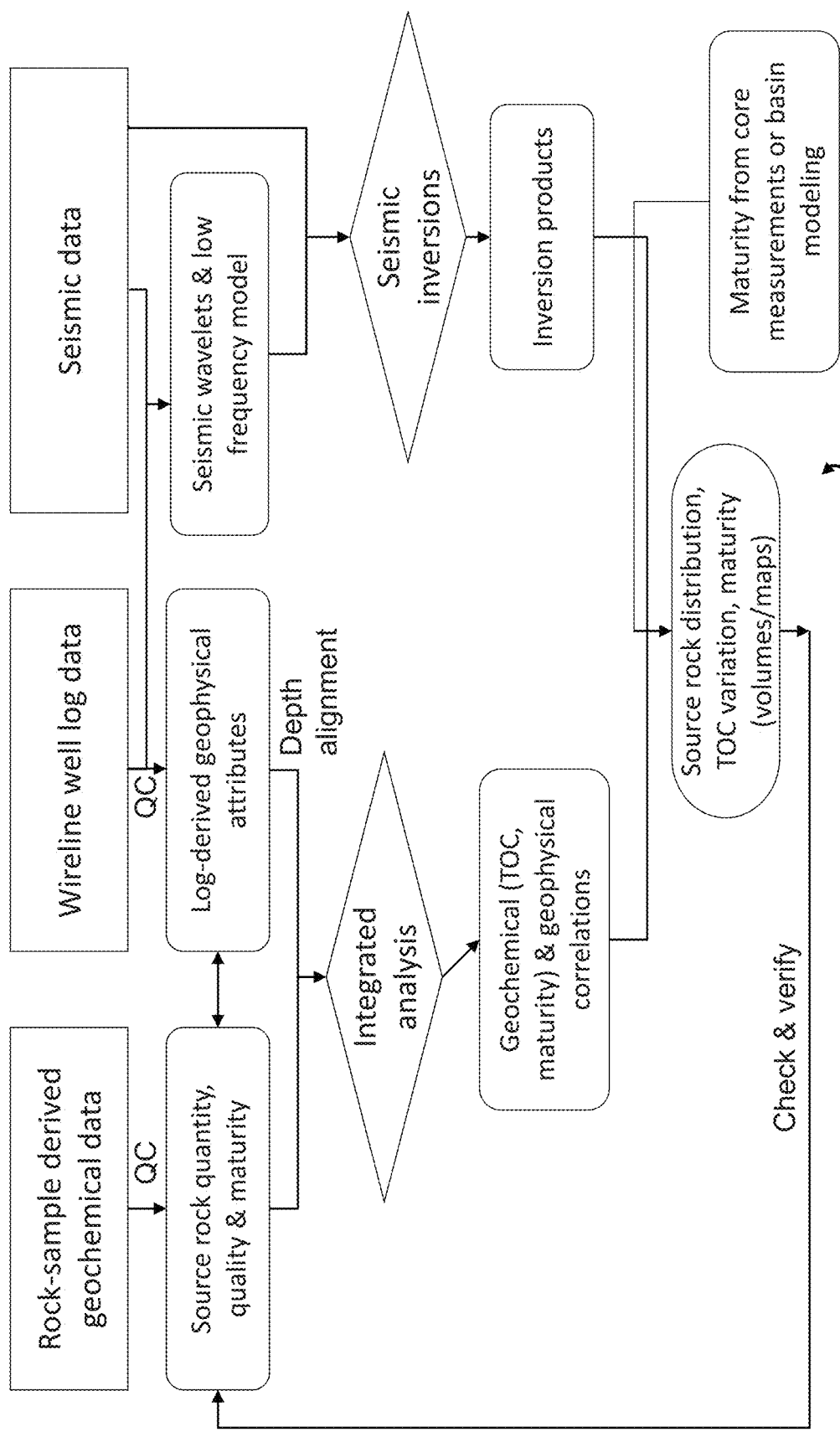
FIG. 15 illustrates a flowchart of a method of source rock characterization, in accordance with some embodiments.
Figure 16:
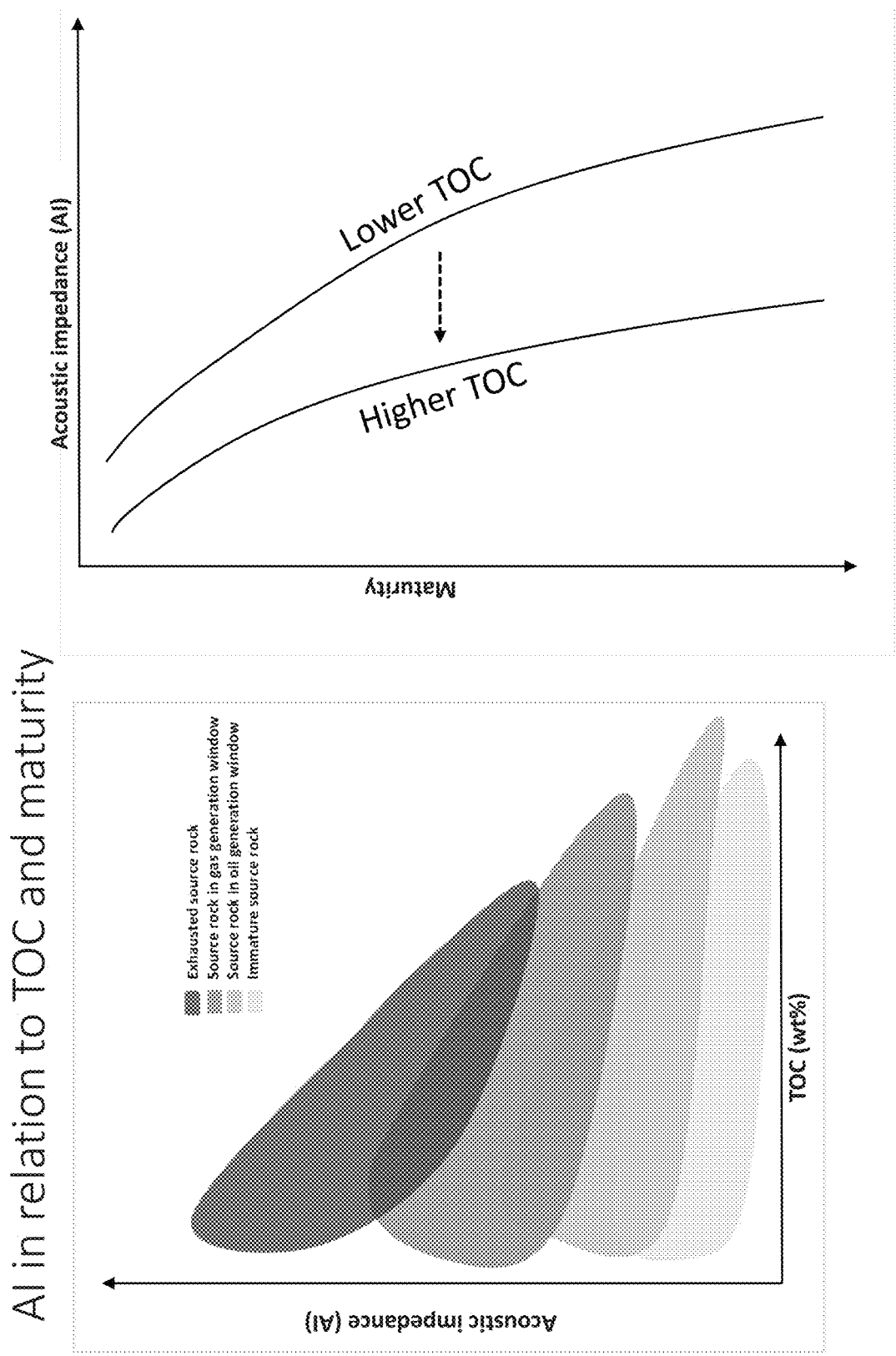
FIG. 16 demonstrates relationships of reservoir properties with depth.
Figure 17:
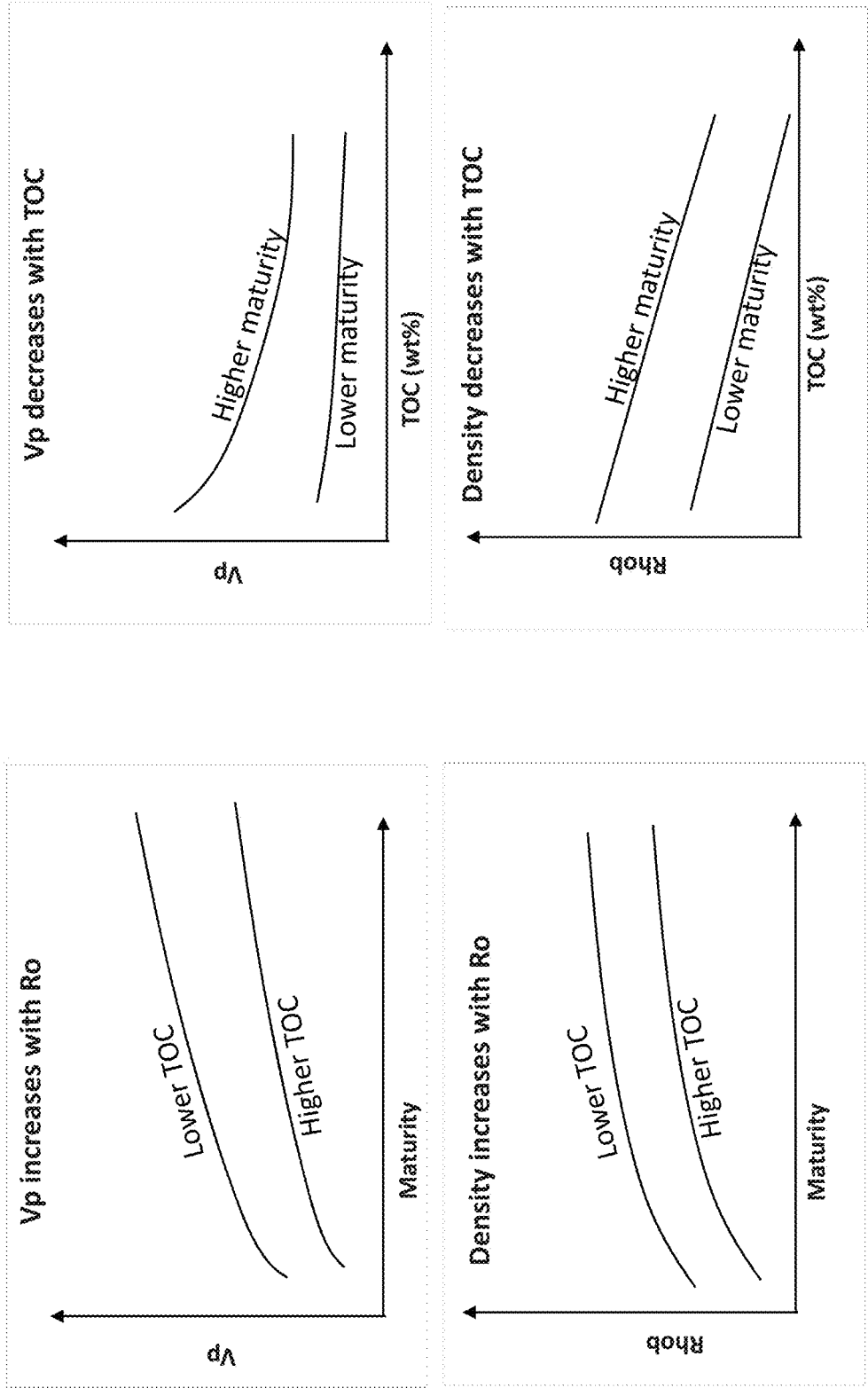
FIG. 17 demonstrates relationships of reservoir properties with depth.

A variation of the method 200 may further be used to estimate the maturity of the source rocks. Referring to FIG. 15, a flowchart for a comprehensive method of source rock characterization 1500 that generates maps of source rock maturity is shown. Method 1500 is similar to method 100 of FIG. 1 but adds input of source rock maturity from core measurements or from basin modeling. As seen in FIG. 16, it is observed that increasing maturity is associated with higher velocity and higher AI. This is likely because the source rock of higher maturity has been exposed to higher compaction and higher temperature resulting more rigid rock framework. As shown in FIG. 17, the relationship between Vp, TOC, and maturity Ro can be determined from well data. Velocity volumes can be estimated from seismic using a number of velocity analysis approaches such as tomography and full-waveform inversion. If TOC is also known in the area, then maturity can be predicted using Vp and TOC as input.

Figure 18:
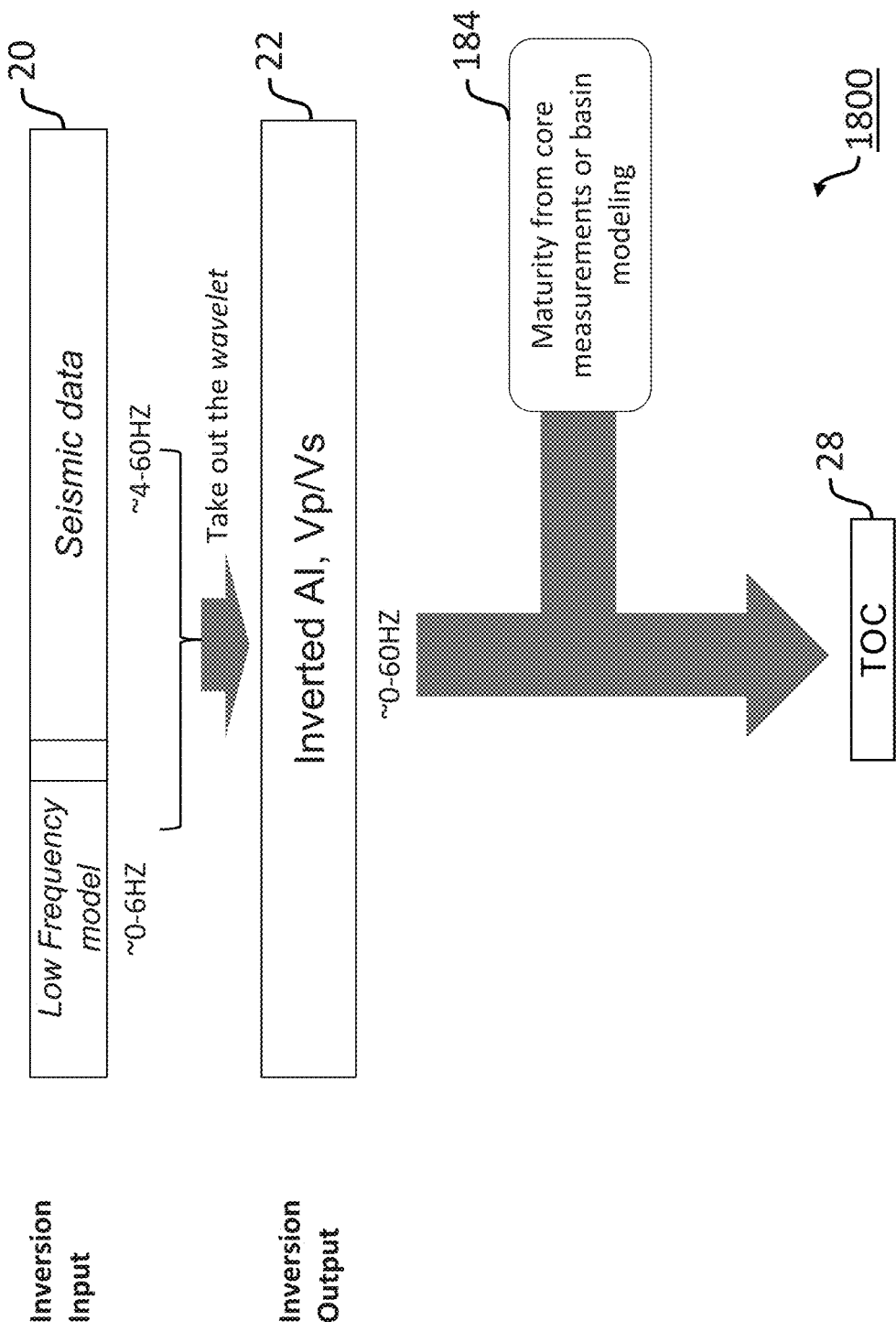
FIG. 18 illustrates a flowchart of steps in a method of source rock characterization, in accordance with some embodiments.
Figure 19:
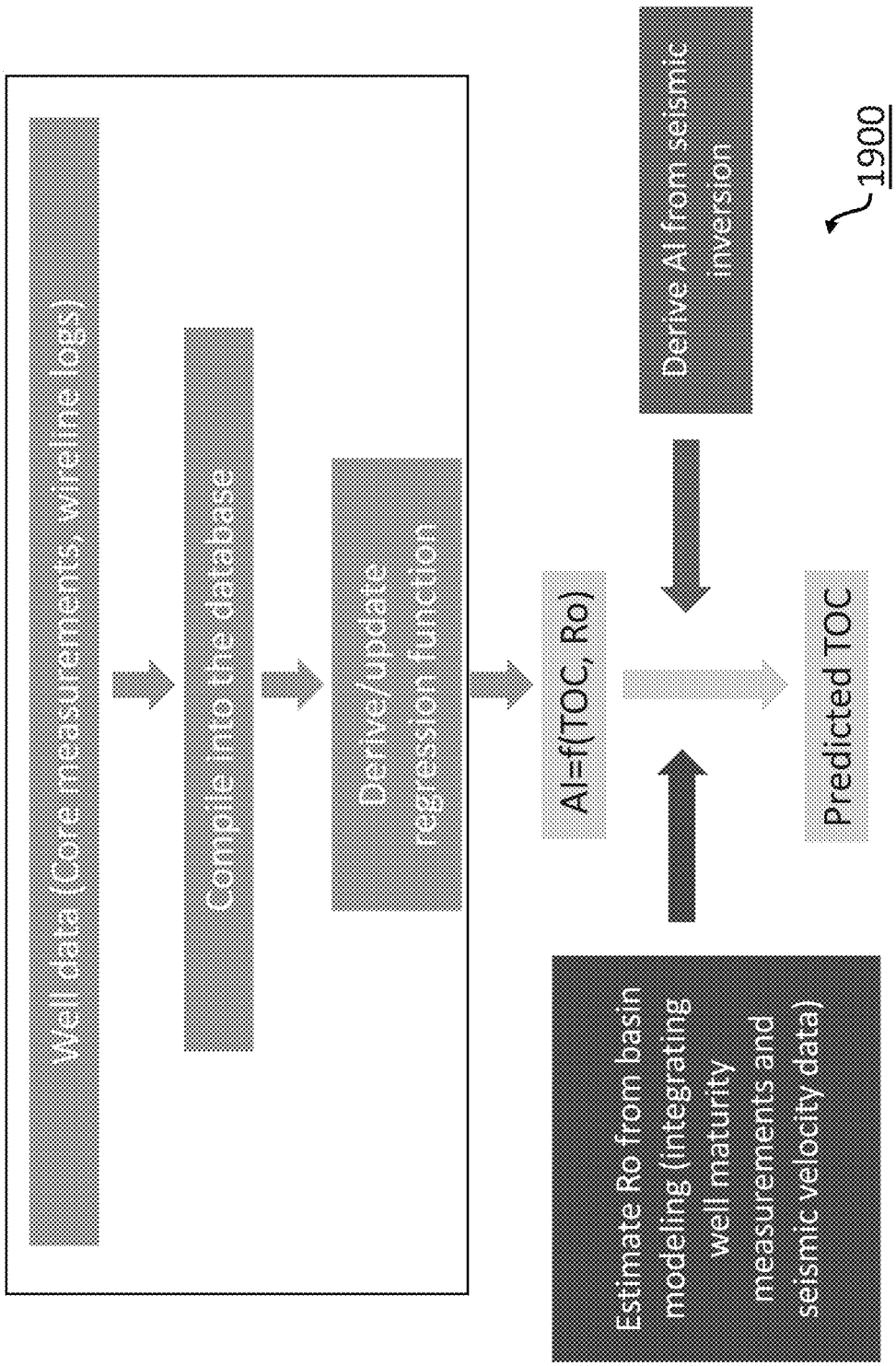
FIG. 19 illustrates a flowchart of steps in a method of source rock characterization, in accordance with some embodiments.
Figure 20:
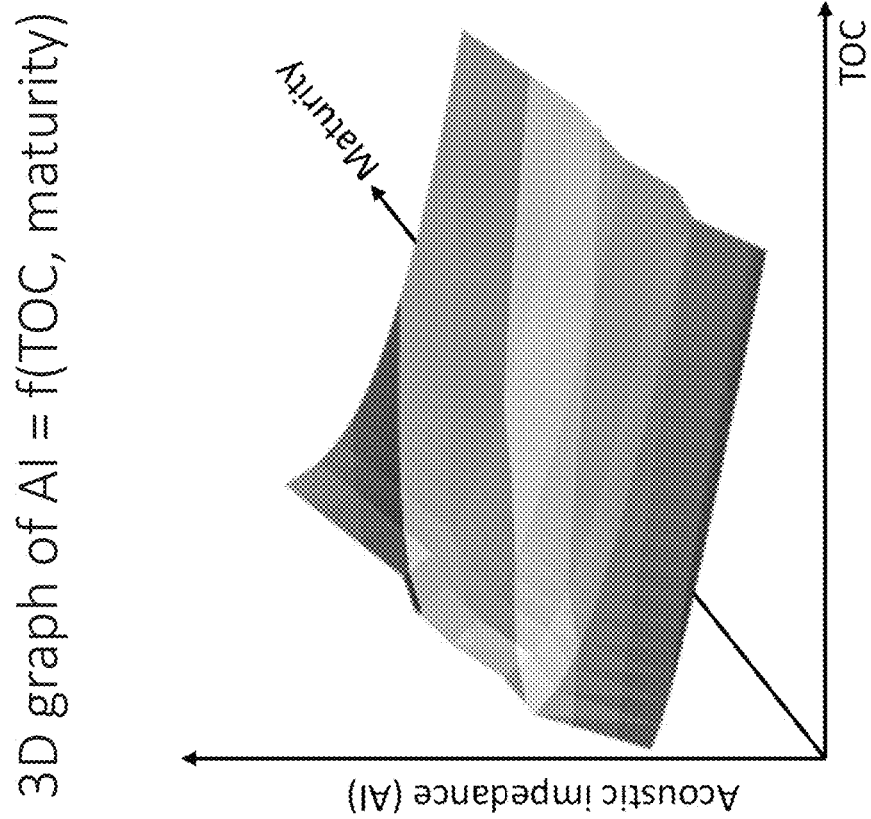
FIG. 20 illustrates a result of embodiments of the present invention.

Similarly, the function between AI, TOC and maturity derived from well data can also be used to predict TOC if AI and thermal maturity are known. FIG. 18 illustrates a method 1800 that is a variation of method 200 from FIG. 2. The low frequency model and seismic data are used as inversion input 20 which is inverted to take out the wavelet and generate inversion output 22 (AI and Vp/Vs). The inversion output 22 can then be combined with thermal maturity from rock measurements or basin modeling results 184 based on the relationships demonstrated in FIG. 16 and FIG. 17 to generate maps or volumes of TOC 28. This variation is further explained in FIG. 19 as method 1900. In method 1900, the well data from rock measurements and/or wireline logs) are compiled into a database so that a regression function can be derived or updated, for example using an analysis of the plots in FIG. 16 or FIG. 17. This function is defined as AI=f(TOC, Ro). The maturity proxy of vitrinite reflectance (Ro) can either be measured from rock samples or be approximated from basin modeling results, and combined with the AI derived from seismic inversion and the function AI=f(TOC, Ro) to generate maps and/or volumes of predicted TOC. This function AI=f(TOC, Ro) is illustrated, for example, in FIG. 20.

It should also be noted that the function can be rewritten as Ro=f(AI, TOC) or Ro=f(Vp, TOC). In this way, the function can be used to estimate thermal maturity Ro from a TOC volume and Vp or AI volume.

Figure 21:
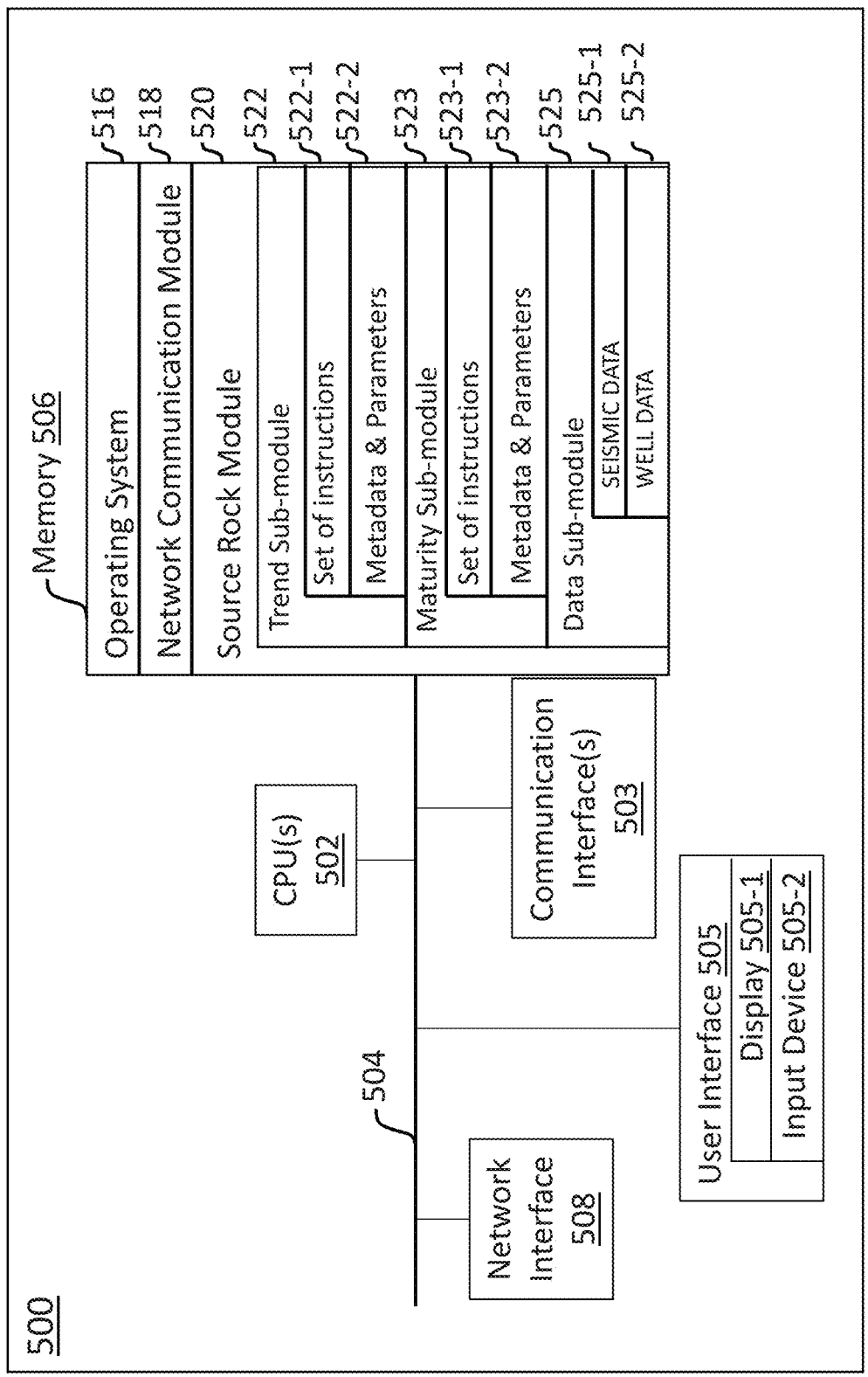
FIG. 21 is a block diagram illustrating a source rock characterization system, in accordance with some embodiments.

FIG. 21 is a block diagram illustrating a source rock characterization system 500, in accordance with some embodiments. While certain specific features are illustrated, those skilled in the art will appreciate from the present disclosure that various other features have not been illustrated for the sake of brevity and so as not to obscure more pertinent aspects of the embodiments disclosed herein.

To that end, the source rock characterization system 500 includes one or more processing units (CPUs) 502, one or more network interfaces 508 and/or other communications interfaces 503, memory 506, and one or more communication buses 504 for interconnecting these and various other components. The source rock characterization system 500 also includes a user interface 505 (e.g., a display 505-1 and an input device 505-2). The communication buses 504 may include circuitry (sometimes called a chipset) that interconnects and controls communications between system components. Memory 506 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 506 may optionally include one or more storage devices remotely located from the CPUs 502. Memory 506, including the non-volatile and volatile memory devices within memory 506, comprises a non-transitory computer readable storage medium and may store seismic data, well data, core data, and/or other geologic information.

In some embodiments, memory 506 or the non-transitory computer readable storage medium of memory 506 stores the following programs, modules and data structures, or a subset thereof including an operating system 516, a network communication module 518, and a source rock module 520.

The operating system 516 includes procedures for handling various basic system services and for performing hardware dependent tasks.

The network communication module 518 facilitates communication with other devices via the communication network interfaces 508 (wired or wireless) and one or more communication networks, such as the Internet, other wide area networks, local area networks, metropolitan area networks, and so on.

In some embodiments, the source rock module 520 executes the operations of method 200, method 1800 and/or 1900. Source rock module 520 may include data sub-module 525, which handles the seismic data 525-1 and well data 525-2. This data is supplied by data sub-module 525 to other sub-modules.

Trend sub-module 522 contains a set of instructions 522-1 and accepts metadata and parameters 522-2 that will enable it to at least generate the seismic attribute Trend-Normalized Reflectivity. The maturity function sub-module 523 contains a set of instructions 523-1 and accepts metadata and parameters 523-2 that will enable it to calculate the maturity of potential source rocks. Although specific operations have been identified for the sub-modules discussed herein, this is not meant to be limiting. Each sub-module may be configured to execute operations identified as being a part of other sub-modules, and may contain other instructions, metadata, and parameters that allow it to execute other operations of use in processing seismic data, well data, and generating images. For example, any of the sub-modules may optionally be able to generate a display that would be sent to and shown on the user interface display 505-1. In addition, any of the data or processed data products may be transmitted via the communication interface(s) 503 or the network interface 508 and may be stored in memory 506.

Methods 200, 1800, and/or 1900 are, optionally, governed by instructions that are stored in computer memory or a non-transitory computer readable storage medium (e.g., memory 506 in FIG. 21) and are executed by one or more processors (e.g., processors 502) of one or more computer systems. The computer readable storage medium may include a magnetic or optical disk storage device, solid state storage devices such as flash memory, or other non-volatile memory device or devices. The computer readable instructions stored on the computer readable storage medium may include one or more of: source code, assembly language code, object code, or another instruction format that is interpreted by one or more processors. In various embodiments, some operations in each method may be combined and/or the order of some operations may be changed from the order shown in the figures. For ease of explanation, the methods are described as being performed by a computer system, although in some embodiments, various operations of method 200 are distributed across separate computer systems.

While particular embodiments are described above, it will be understood it is not intended to limit the invention to these particular embodiments. On the contrary, the invention includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Although some of the various drawings illustrate a number of logical stages in a particular order, stages that are not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

REFERENCES

Chen, 2016, U.S. Pat. No. 10,120,092
Loseth H. et al., 2011, Geology, Can hydrocarbon source rocks be identified on seismic data? pp. 1167-1170
Vernik, L. and Milovac, J., 2011, The Leading Edge, Rock physics of organic shales. pp. 318-323
Bandyopadhyay, K., et al., 2012, SEG Annual Meeting Abstract, Rock Property Inversion in Organic-Rich Shale: Uncertainties, Ambiguities, and Pitfalls. pp. 1-5
Loseth et al, 2016, U.S. Pat. No. 9,244,182, Method of assessing hydrocarbon source rock candidate.

What is claimed is:

1. A computer-implemented method of hydrocarbon source rock characterization, comprising:
   a. receiving, at a computer processor, a seismic dataset representative of a subsurface volume of interest and a low frequency model of the subsurface volume of interest;
   b. inverting, via the computer processor, the seismic dataset using the low frequency model to generate reservoir attributes;
   c. receiving, at the computer processor, maturity data from core measurements or basin modeling; and
   d. characterizing, via the computer processor, the hydrocarbon source rock based on the reservoir attributes and maturity data wherein the characterizing includes at least one of deriving a function AI=f(TOC, Ro), deriving a function Ro=f(AI, TOC), or deriving a function Ro=f(Vp, TOC), wherein AI is acoustic impedance, TOC is Total Organic Content, Ro is vitrinite reflectance, and Vp is compressional velocity.

2. The method of claim 1 wherein the reservoir attributes include acoustic impedance and compressional velocity (Vp) shear velocity (Vs) ratio.

3. The method of claim 1 wherein the characterizing includes one or more of estimated TOC, source rock location, source rock thickness, and source rock maturity.

4. A computer system, comprising:
   one or more processors;
   memory; and
   one or more programs, wherein the one or more programs are stored in the memory and configured to be executed by the one or more processors, the one or more programs including instructions that when executed by the one or more processors cause the system to:
   a. receive, at the one or more processors, a seismic dataset representative of a subsurface volume of interest and a low frequency model of the subsurface volume of interest;
   b. invert, via the one or more processors, the seismic dataset using the low frequency model to generate reservoir attributes;
   c. receive, at the one or more processors, maturity data from core measurements or basin modeling; and
   d. characterize, via the one or more processors, the hydrocarbon source rock based on the reservoir attributes and maturity data wherein the characterizing includes at least one of deriving a function AI=f(TOC, Ro), deriving a function Ro=f(AI, TOC), or deriving a function Ro=f(Vp, TOC), wherein AI is acoustic impedance, TOC is Total Organic Content, Ro is vitrinite reflectance, and Vp is compressional velocity.

5. The system of claim 4 wherein the characterizing includes one or more of estimated TOC, source rock location, source rock thickness, and source rock maturity and wherein the system further generates a 2-D or 3-D map of the one or more of estimated TOC, source rock location, source rock thickness, and source rock maturity.

6. A non-transitory computer readable storage medium storing one or more programs, the one or more programs comprising instructions, which when executed by an electronic device with one or more processors and memory, cause the device to:

a. receive, at the one or more processors, a seismic dataset representative of a subsurface volume of interest and a low frequency model of the subsurface volume of interest;

b. invert, via the one or more processors, the seismic dataset using the low frequency model to generate reservoir attributes;

c. receive, at the one or more processors, maturity data from core measurements or basin modeling; and d. characterize, via the one or more processors, the hydrocarbon source rock based on the reservoir attributes and maturity data wherein the characterizing includes at least one of deriving a function AI=f(TOC, Ro), deriving a function Ro=f(AI, TOC), or deriving a function Ro=f(Vp, TOC), wherein AI is acoustic impedance, TOC is Total Organic Content, Ro is vitrinite reflectance, and Vp is compressional velocity.

7. The device of claim 6 wherein the characterizing includes one or more of estimated TOC, source rock location, source rock thickness, and source rock maturity and wherein the system further generates a 2-D or 3-D map of the one or more of estimated TOC, source rock location, source rock thickness, and source rock maturity.

* * * * *